(12) United States Patent
McMillan et al.

(10) Patent No.: US 6,240,925 B1
(45) Date of Patent: Jun. 5, 2001

(54) PHOTOTHERMAL VASCULAR TARGETING WITH BIOREDUCTIVE AGENTS

(75) Inventors: Kathleen McMillan, Concord; Frederic M. Durville, Chelmsford, both of MA (US)

(73) Assignees: Cynosure, Inc., Chelmsford; New England Medical Center Hospitals, Inc., Boston, both of MA (US)

( * ) Notice: Subject to any disclaimer, the term of this patent is extended or adjusted under 35 U.S.C. 154(b) by 0 days.

(21) Appl. No.: 09/274,576

(22) Filed: Mar. 23, 1999

(51) Int. Cl.[7] .................................................. A61B 19/00
(52) U.S. Cl. ................................................ 128/898; 600/1
(58) Field of Search .............................. 128/898; 600/1, 600/2, 3, 4

(56) References Cited

U.S. PATENT DOCUMENTS 4,889,525 * 12/1989 Yuhas et al. ............................ 600/1
5,066,293   11/1991 Furumoto ................................ 606/9
5,257,970   11/1993 Dougherty ............................ 604/20
5,312,395    5/1994 Tan et al. ................................ 606/9
5,346,488    9/1994 Prince et al. ........................... 606/7
5,749,868    5/1998 Furumoto ................................ 606/9

OTHER PUBLICATIONS

Anderson et al., "Selective Photothermolyisis: Precise Microsurgery by Selective Absorption of Pulsed Radiation," *Science*, 220(4596):524–527 (1983).

Spears et al., "Fluorescence of Experimental Atheromatous Plaques with Hematoporphyrin Derivative," *J. Clin. Invest*, 71:395–399 (1983).

* cited by examiner

*Primary Examiner*—Dinh X. Nguyen
(74) *Attorney, Agent, or Firm*—Banner & Witcoff, Ltd.

(57) ABSTRACT

A method of selectively enhancing the effect of photothermal vascular targeting on tumor regression by administration of a bioreductive agent is disclosed.

20 Claims, 5 Drawing Sheets

PHOTOTHERMAL VASCULAR TARGETING WITH BIOREDUCTIVE AGENTS

BACKGROUND OF THE INVENTION

1. Field of the Invention

Embodiments of the present invention relate in general to the combined use of laser therapy and cytotoxic agents in the treatment of vascular lesions including tumors. More particularly, embodiments of the present invention relate to methods of reducing or eliminating growth of tumors using laser light and bioreductive agents without significant harm to surrounding normal tissue.

2. Description of Related Art

Vascular targeting is an anticancer strategy in which the endothelial wall of the blood vessels supplying the tumor is the treatment target, and tumor cell hypoxia is a therapeutic goal. Because of the interdependence of tumor cells and tumor vasculature, prolonged ischemia secondary to irreversible loss of tumor blood vessel function will result in tumor cell necrosis. Vascular targeting has as its goal the destruction of existing tumor vasculature and so differs from anti-angiogenic therapies aimed at preventing the growth of new vessels within a tumor.

The function of the tumor vascular supply has significance both in the natural progression of a malignancy and in the outcome of treatment. The chaotic vascular architecture and abnormalities of blood flow within tumor microvessels are associated with regions of tumor hypoxia that limit the efficacy of both chemotherapy and radiotherapy. Similarly, the effectiveness of photodynamic therapy depends on an adequate oxygen level within the tumor for generation of cytotoxic species.

The application of phototherapy to tumor treatment has been actively pursued because of both the incidence and health significance of tumors that arise in the skin or mucosal surfaces, including the gastrointestinal tract, aerodigestive tract, urinary bladder, and cervix, and therefore are readily accessible to radiation. The phototherapeutic approach typically involves administering a photosensitizer, allowing a suitable period of time for uptake of this photosensitizer by the tumor tissue, and irradiation at a wavelength absorbed by the photosensitizer to produce cytotoxic species. Although preferential accumulation of photosensitizer in tumor versus normal tissue has been demonstrated for certain photosensitizers, prevention of damage to normal vasculature typically requires spatial confinement of the irradiated zone to the target tumor tissue.

When the photosensitizer is administered intravenously, it has been observed that vascular damage follows irradiation. This vascular damage has been exploited in ophthalmology for treatment of pathologic ocular neovascularization and in dermatology for treatment of benign vascular lesions. Photodynamic therapy specifically designed to target tumor vasculature has been described. However, the mechanism of photodynamic therapy leads to vascular damage in any tissue that is exposed to radiation, in the presence of sufficient oxygen. Tumor blood vessels and the vessels supplying normal tissue surrounding the tumor are both susceptible to damage by the cytotoxic species produced by the intravenous photosensitizer during illumination.

Selective photothermolysis is a method of causing selective and irreversible photothermal damage to tissue structures containing a chromophore that can be used to distinguish that target structure from surrounding tissue. For a light source, typically a laser, to be useful for selective photothermolysis, it must emit with sufficient intensity at a wavelength preferentially absorbed by the target chromophore. The pulse duration or exposure time of the source must be less than the thermal relaxation time of the target, to minimize temperature increases in tissue surrounding the target. Techniques based on this concept using well known laser systems are well established for treatment of benign cutaneous vascular lesions such as portwine stain (PWS), birthmarks, telangiectasias, hemangiomas, warts, psoriasis, arthritis in which hemoglobin in the abnormal, ectatic lesional vasculature serves as the chromophore and the target is the vessel wall, as well as, atherosclerotic plaque and other desired applications. See U.S. Pat. No. 5,312,395; U.S. Pat. No. 5,749,868; U.S. Pat. No. 5,257,970; U.S. Pat. No. 5,066,293, U.S. Pat. No. 5,346,488, "Selective Photothermolysis: Precise Microsurgery by Selective Absorption of Pulsed Radiation", Anderson et al., Science, 220:524–527 (1983); Spears et al. *J. Clin. Invest*, 71, 39–399 (1983) each of which are hereby incorporated by reference in their entireties for all purposes. The deepest blood vessels contributing to the color of PWS lesions are approximately 1 mm below the skin surface, and are accessible to selective photothermal targeting using available lasers such as the 585 nm pulsed dye laser. The theoretical advantages of selective photothermolysis have been borne out in clinical studies showing that PDL treatment of benign cutaneous vascular lesions is associated with very low risk of scarring. However, photothermolysis techniques would be more effective if the results of damage to surrounding tumor vasculature and other blood vessels primarily responsible for maintaining growth of the tumor could be advantageously used to promote the efficacy of cytotoxic agents which are activated by hypoxic conditions produced as a result of tumor vascular damage.

Accordingly, there is a need in the art to provide methods of treating tumors combining photothermolysis and cytotoxic species that are activated under hypoxic conditions. There is also a further need in the art to selectively localize the effects of photothermolysis to target tumors and their associated microvasculature without significantly harming surrounding normal tissue.

BRIEF SUMMARY OF THE INVENTION

Embodiments of the present invention are directed to methods in mammals including a human which are useful in selectively treating tumors or other vascular lesions surrounded by normal or otherwise healthy tissue without significantly harming or otherwise adversely affecting the surrounding normal tissue. A tumor is treated according to the invention in a manner to reduce or regress existing tumor size, to inhibit the growth of an existing tumor or to prevent establishment of a vascularized tumor mass. According to the methods of the present invention, a tumor or other area selected for treatment is irradiated with laser light having a wavelength, duration, fluence and spot size selected to preferentially heat blood vessels that supply the tumor with sufficient blood and oxygen to support its growth in the presence of a bioreductive agent or hypoxic cytotoxin. According to one embodiment, the blood vessels are heated to the point of denaturation and to effectively prevent blood and oxygen flow through the blood vessels to the tumor, thereby depriving the tumor of nourishment and accordingly leading to tumor necrosis, reduction or regression of tumor size, inhibit of the growth of an existing tumor or prevention of establishment of a vascularized tumor mass. In general, according to the present invention, the blood vessels are heated as a result of irradiation in a manner to create a region of hypoxia, i.e. reduced oxygen content.

According to one embodiment of the present invention, a chromophore, such as a dye, or other photoactive agent is administered to the site of irradiation. The chromophore acts to selectively absorb the chosen wavelength of laser light thereby enhancing the effectiveness of the irradiation. Other chromophores or photoactive compounds can be used which themselves act as therapeutic or cytotoxic agents upon irradiation.

Methods of the present invention also include the administration of a cytotoxic agent or hypoxic cytotoxin which is preferentially activated under conditions of hypoxia to effectively prevent or eliminate tumor growth or reduce tumor size or otherwise lead to tumor necrosis, or otherwise prevent establishment of a vascularized tumor mass. Such cytotoxic agents or hypoxic cytotoxins are commonly known as bioreductive agents. According to the present invention, a method of treating a tumor characterized by nutrient-providing blood vessels is provided including irradiating the tumor or nutrient providing blood vessels in the presence of a bioreductive agent, providing an environment of hypoxia for the bioreductive agent, and allowing the bioreductive agent to act as a cytotoxic agent in a manner to effectively reduce tumor size, eliminate tumor growth or otherwise lead to tumor necrosis, or otherwise prevent establishment of a vascularized tumor mass.

Other features and advantages of certain embodiments of the present invention will become more fully apparent from the following description taken in conjunction with the accompanying figures and claims,

BRIEF DESCRIPTION OF THE DRAWINGS

In the course of the detailed description of certain preferred embodiments to follow, reference will be made to the attached figures, in which.

DETAILED DESCRIPTION OF CERTAIN PREFERRED EMBODIMENTS

The principles of the present invention may be applied with particular advantage to treat tumors or other lesions which have associated blood vessels which provide nourishment to the tumor or other lesion. According to the teachings of the present invention, a tumor is irradiated with a laser light source having a wavelength, duration, fluence and spot size sufficient to render blood vessels associated with the tumor incapable of providing continued and sufficient blood and/or oxygen for sustained or continued growth.

In one embodiment, the laser light is produced by a tunable pulsed dye laser system and is characterized in having a wavelength corresponding to that which is absorbed by hemoglobin found in the blood vessels. The wavelength produced by the pulsed dye laser is well absorbed by oxyhemoglobin in blood, and its pulse duration (300 to 500 $\mu s$) is short enough that heat is largely confined to ectatic microvessels during the laser pulse. Consequently, irreversible vascular damage may be achieved with little or no damage to surrounding tissue structures.

In general, suitable pulsed dye laser systems useful in the present invention include a power source, a flashlamp capable of emitting multiple pulses of light, a dye reservoir containing a dye suitable for stimulated emission of light, and an optical resonator having an output coupler. The power source, flashlamp, dye reservoir and optical resonator are operatively connected so as to generate multiple pulses of laser light having a defined wavelength and pulse duration. An optical fiber is operatively coupled to the optical resonator in a manner to allow the multiple pulses of laser light to travel from the optical resonator through the optical fiber to the tumor or tissue margin area to be irradiated with a defined pulse fluence. A handpiece delivery system incorporating the terminal end of the optical fiber is used to effectively direct the laser light source to the target area in the mammal.

According to one embodiment, useful wavelengths are between about 560 nm to about 610 nm, preferably between about 570 nm to about 600 nm and more preferably about 585 nm or about 590 nm. The laser light has a pulse duration less than the thermal relaxation time of the volume of tissue being irradiated. Specific pulse durations include between 0.1 msec to about 60 msec, preferably between 0.1 to about 10 msec and more preferably about 0.3 msec. The delivered fluence of the pulsed laser light is between about 1 $J/cm^3$ to about 30 $J/cm^3$, preferably between about 5 $J/cm^3$ to about 15 $J/cm^3$ and more preferably about 10 $J/cm^3$. The irradiated spot size is sufficient to include the tumor as a whole or portions thereof According to an additional embodiment, the spot size is sufficient to include not only the tumor but an area of normal tissue adjacent to or surrounding the tumor within which is included blood vessels which nourish the tumor with blood and oxygen sufficient for its continued growth. The area of normal tissue adjacent to or surrounding the tumor within which is included blood vessels which nourish the tumor is referred to herein as the "margin" or "margin of tissue". Alternatively, the laser light has a spot size sufficient to irradiate only the margin or portions thereof, or part of the margin and part of the tumor. Spot sizes in accordance with the present invention include those between about 1 mm to about 20 mm, preferably about 5 mm to about 15 mm and more preferably about 10 mm.

It is to be understood that other lasers, such as yellow, green and blue wavelength lasers with or without suitable exogenous chromophores, are useful within the scope of the present invention and include Argon ion lasers, Copper-vapor lasers, alexandrite lasers, ruby lasers, semiconductor diode lasers, frequency-doubled Nd:YAG lasers, and other dye lasers pumped by a Nitrogen laser or Argon-ion laser and the like. The lasers within the scope of the present invention are pulsed but may also operate in a continuous-wave (cw) mode with a scanner to automatically scan the treatment area and provide temporal modulation of the laser intensity on the treatment site.

In addition, one or more exogenous agents and/or dyes are also administered when necessary to enhance the absorption of the laser light at the site of irradiation and to also aid in the selective absorption of laser light. Administration of exogenous chromophores are used to take advantage of the deeper tissue penetration of longer visible or near-infrared wavelengths. Such exogenous chromophores include the lipophilic dye indocyanine green (ICG) and the like. One or more photoactivated compounds can also be administered as necessary to therapeutically treat the tumor. The amount, duration and mode of administration of the chromophore or other photoactive agent will depend on its properties and the makeup of the individual on which the treatment is to be carried out. Typically, between about a 50 mg and about a 2000 mg, preferably 500 mg dose of ICG for a patient of 100 kg of body weight is injected intravenously to the patient immediately prior to laser irradiation.

According to the present invention, the area of the individual to be treated should be irradiated at least once with laser light having the above parameters, with the appropriate number of pulses necessary to treat the entire area. When deeper penetration of the laser light is desired, the area may be irradiated several times, and the complete treatment may be repeated up to five times with at least one week between each treatment.

The potential advantage of selective photothermal vascular targeting over conventional anticancer strategies is the preservation of normal tissue surrounding the tumor. The basis of the ability of photothermal techniques to discriminate between lesion and normal skin may be due to differences in size between pathologic and normal cutaneous vasculature; it is known that for effective and selective photothermal injury to the vessel wall the pulse duration of the laser should be equal to or slightly less than the thermal relaxation time of the targeted vessel. According to the present invention, a small margin of skin at the tumor periphery is irradiated. While not wishing to be bound to any scientific theory, this peripheral region or "margin" is believed to be the location of relatively large caliber vessels that supply and drain the tumor microvasculature. Successful tumor treatment may be the result of selective damage to the arterioles and venules at the periphery, rather than direct damage to the much smaller capillaries, i.e. microvasculature, within the tumor itself. The existence of large caliber feeding vessels as an integral part of the tumor microvascular architecture has been documented in corrosion cast studies of human colorectal carcinomas, cutaneous basal cell tumors, and xenotransplanted human tumors grown in mice. Other factors may be at work, for example the relative fragility of tumor microvasculature and the closer dependence of proliferating tumor cells on their vascular supply.

According to the invention, the blood and oxygen supplying vessels of a tumor are irradiated to the extent to cause irreversible ischemic damage to tumor cells but also in a manner to spare normal surrounding tissue. This method is implemented, depending on the size and depth of the tumor and its vascular architecture, by means of the pulsed dye laser or any other source of radiation preferentially absorbed by the endogenous chromophores of blood, or by use of other, more deeply penetrating radiation sources in combination with an exogenous chromophore such as ICG.

According to an addition embodiment of the present invention, one or more bioreductive agents are administered to enhance the effect of photothermal vascular targeting on tumor regression. Bioreductive agents according to the present invention include porfiromycin (POR), mitomycin C, tirapazamine, indoloquinone and the like. POR is a prodrug that is activated by bioreductive enzymes in the absence of oxygen to form cytotoxic species. Mitomycin C, which is structurally related to POR, is also a useful bioreductive agent within the scope of the present invention. The preferential toxicity for hypoxic cells is greater for POR than mitomycin C.

The following examples are set forth as representative of the present invention. These examples are not to be construed as limiting the scope of the invention as these and other equivalent embodiments will become apparent in view of the present disclosure, figures and accompanying claims.

EXAMPLE I

Cell Culture

KB cells (human pharyngeal SCC, American Type Culture Collection, Rockville, Md.) were maintained in culture medium consisting of 90% Minimal Essential medium (Gibco BRL, Grand Island, N.Y.) and 10% fetal bovine serum (Hyclone, Logan, Utah) with the addition of 10 nM nonessential amino acid (Gibco BRL) and antibiotics (penicillin, streptomycin: Gibco BRL). The cells were grown as monolayers in Falcon T150 flasks (Becton Dickinson, Franklin Lakes, N.J.) in a 37° C. humidified incubator with 5% $CO_2$.

Prior to inoculation, the cells were rinsed with PBS lacking calcium and magnesium (Gibco BRL), trypsinized (Gibco BRL), counted, centrifuged at 1000 rpm for 6 min., and resuspended in normal saline for a final concentration of 1,000,000 cells/ml.

EXAMPLE II

Tumor Model

Six- to seven-week-old nude mice (Charles River Labs, Wilmington, Mass.) were sterilely housed and fed ad libitum. Intradermal inoculation of 0.05 ml of cell suspension (50,000 cells) was performed under general anesthesia (ether) using a 30 gauge hypodermic needle. After 5 days, the majority of the tumors were visually apparent and palpable.

EXAMPLE III

Statistical Analysis

The effect of treatment on tumor volumes was determined using analysis of variance. Multiple comparisons were performed using the Student-Newman-Keuls (SNK) test. P values less than 0.05 are considered significant.

EXAMPLE IV

Effect of POR Alone

Fifteen mice, each with 4 tumor inoculations, were divided into 4 treatment groups and 1 control group. Five days after tumor inoculation, the 4 treatment groups received 2.50, 5.0, 7.5, and 10.0 mg/kg intraperitoneal (ip) injections of POR (Vion Pharmaceuticals, Inc., New Haven, Conn.) dissolved in sterile water. (The $LD_{50}$ of POR in mice is 50 mg/kg.) The control group received ip saline injections. The 3 orthogonal diameters of the tumors were measured at days 0, 2, 4, 6, 8, 10, and 13 following POR injection. All measurements included the thickness of the overlying skin. All mice were anesthetized during ip injections and tumor measurements. The tumor volume was estimated as the product of the three orthogonal diameters multiplied by $\pi/6$. The mice were weighed at the time of each tumor measurement to monitor for any systemic toxicity of POR.

Figure 1:
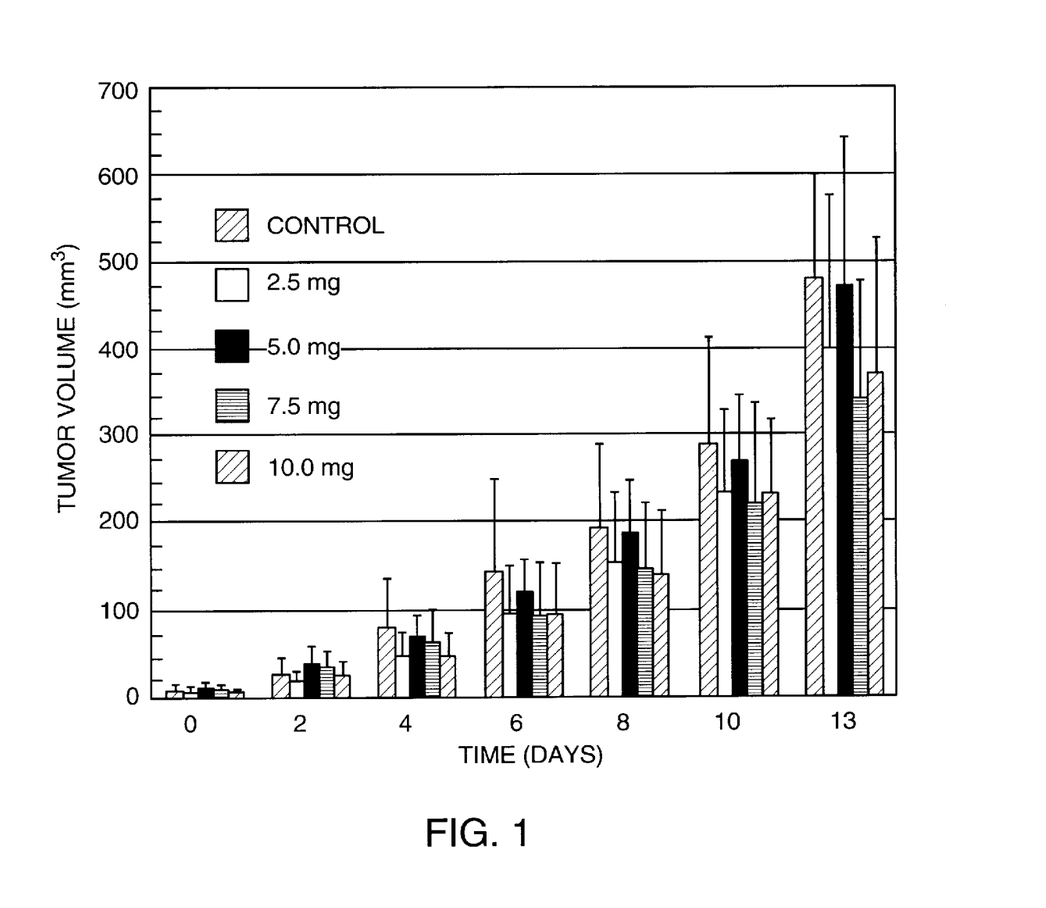
FIG. 1 is a graph of mean tumor volumes of experimental mouse groups as a function of time after administration of different dosages of the bioreductive agent porfiromycin (POR). Error bars indicate +1 standard deviation.

FIG. 1 shows the mean tumor volumes of each experimental group as a function of time after the administration of POR. Analysis of variance indicates no significant effect of treatment at any point in time. There is also no significant effect of treatment on body weight, or any other indication of acute toxicity related to POR administration. Tumors ranged in volume at time of treatment on day 0 (5 days after tumor cell inoculation) from 0.5 to 20.9 mm$^3$, with a mean volume of 8.2 mm$^3$ and standard deviation (SD) of 5.3 mm$^3$.

EXAMPLE V

POR with PDL Limited to Tumor Area

Sixteen mice, each with 4 tumor inoculations, were divided into 3 treatment groups and 1 control group. On day 6 following tumor inoculation, the treatment groups received (1) ip POR only (10 mg/kg), (2) ip saline and PDL limited to tumor area (585 nm, 10 J/cm$^2$, 300–500 $\mu$s; Model SPTL-1a, Candela Corporation, Wayland, Mass.), or (3) ip POR (10 mg/kg) and PDL limited to the tumor area (585 nm, 10 J/cm$^2$, 300–500 $\mu$s). The control group received ip saline injections only. PDL irradiation was performed 15 min. after administration of POR or vehicle, using a laser handpiece that produced a 5 mm diameter irradiated spot with a uniform energy distribution on the tumor surface. An aluminum plate with holes of various diameters was used to shield areas beyond the tumor border. For those tumors larger than 5 mm, multiple partially overlapping exposures were necessary to irradiate the entire tumor area. Treatments were repeated in all groups two days later. The orthogonal diameters of the tumors were measured and the mice were weighed on days 0, 2, 4, 6, 8, 10, and 13 following the first treatment. One mouse from the control group died during anesthesia before day 10 and was therefore excluded from analysis.

Following the final measurement, tumors in control and treatment groups were fixed with formalin, embedded in paraffin, sectioned, and stained with hematoxylin and eosin (H&E) for histologic evaluation.

Figure 2:
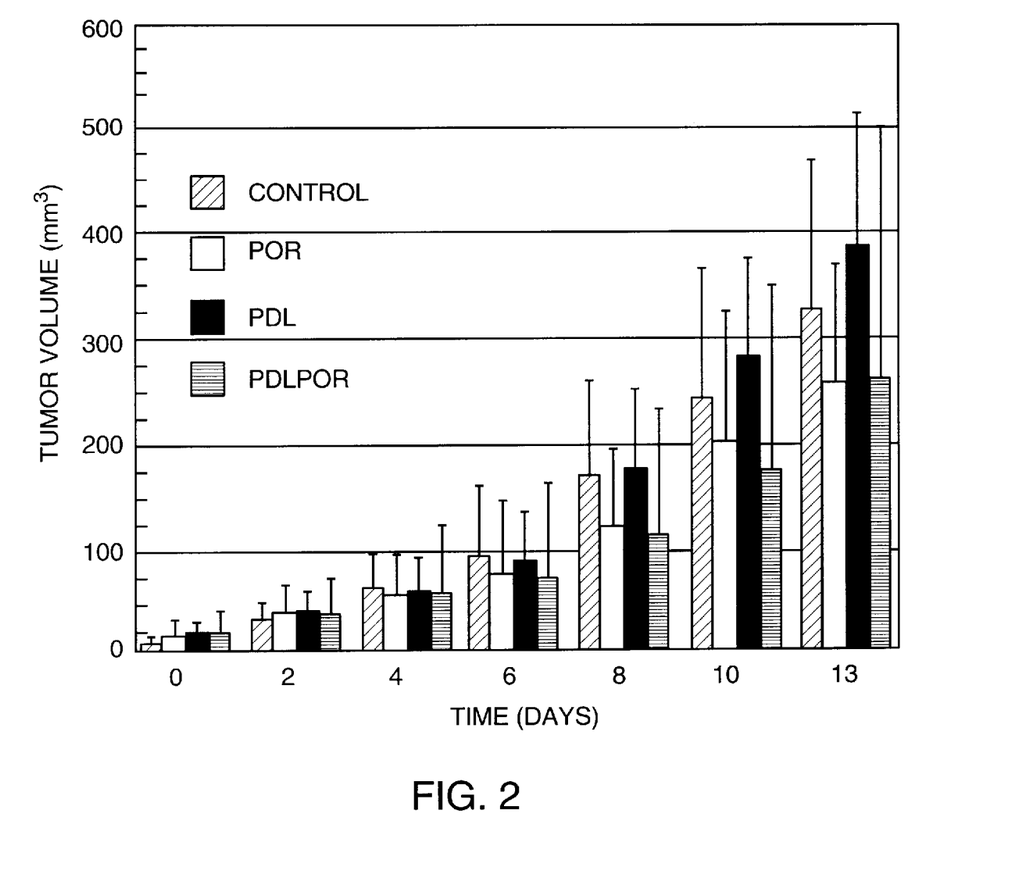
FIG. 2 is a graph of mean tumor volumes of four experimental mouse groups as a function of time after first treatment of the tumor only and excluding the tumor margin, one group including POR only, one group including vascular targeting only, one group including POR with vascular targeting and one control group. Error bars indicate +1 standard deviation.

In Example IV, the difference in growth of tumors in mice receiving POR alone at any dosage within the range tested and the growth of tumors in control mice was not statistically significant, therefore in this Example V any difference between groups receiving PDL treatment with and without POR in this dosage range was expected to indicate supra-additivity. The highest POR dosage tested in Example IV (10 mg/kg) was used to increase the likelihood of detecting a difference between the two laser treatment groups. FIG. 2 shows the mean tumor volumes for each experimental group after the first treatment session At the start of treatment (day 0, 6 days after tumor cell inoculation) the mean volume of all tumors was 14.8 mm$^3$ (SD 12.5 mm$^3$) Analysis of variance indicates no significant effect of treatment at any point in time. There was no gross evidence of skin sloughing or any histological evidence of epithelial necrosis in the laser treatment groups.

Dermal skin flaps containing the tumor masses were examined in 2 animals from control and PDL groups following the final tumor measurement on day 13. While a small portion of the blood supply appeared to originate in the subcutaneous tissue, a notable aspect of the tumors was the presence of radially organized large caliber microvessels in the dermis. It is believed that these supplying vessels had been shielded by the template during PDL irradiation.

EXAMPLE VI

POR with PDL Extending Beyond Tumor Area

Twelve mice with 6 tumor inoculations were divided into 3 treatment groups and 1 control group. On day 5 following inoculation, the 4 groups were treated as in Example V except that the field of irradiation was extended to include a 2 to 3 mm periphery beyond the tumor edge. In addition, on the second treatment day, the fluence was raised from 10 to 15 J/cm$^2$. Tumor volume measurements were performed on days 0, 2, 4, 6, 8, 10, and 12 following the first treatment. Mice were weighed on day 0 and 6 following the first treatment. There were two anesthesia related deaths: one mouse from the control group and one mouse from the group receiving both PDL and POR died before day 10 and were therefore excluded from analysis.

Following the final tumor measurement, control tumors, residual treated tumors, and areas previously exhibiting tumors were processed as before for histologic evaluation.

Figure 3:
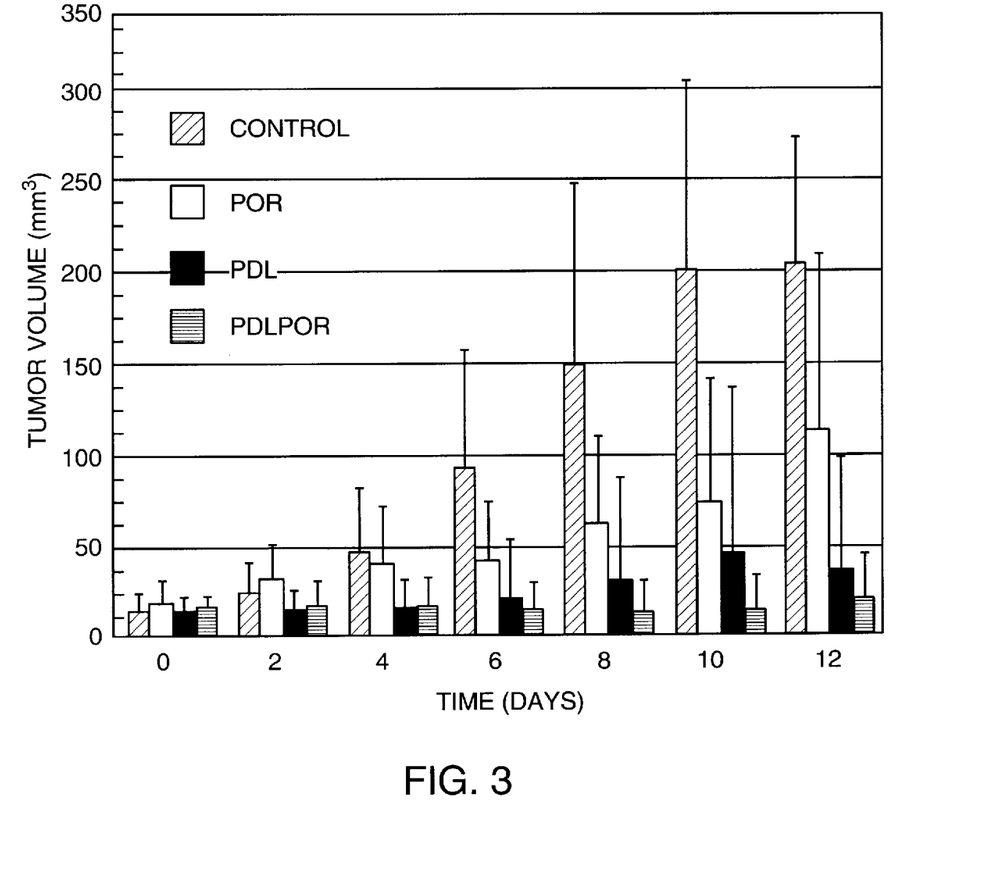
FIG. 3 is a graph of mean tumor volumes of four experimental mouse groups as a function of time after first treatment of the tumor and tumor margin, one group including POR only, one group including vascular targeting only, one group including POR with vascular targeting and one control group. Error bars indicate +1 standard deviation.

When PDL treatment was extended to a small margin of tissue beyond the tumor edge encompassing the supply vessels, tumor growth was significantly affected as shown in FIG. 3. At the time of treatment, the mean volume of all tumors was 15.2 mm$^3$ (SD 8.3 mm$^3$). An effect of treatment was seen at all days beginning with day 2 (day 2, $p<0.05$; day 4, $p<0.01$, days 6 through 13, $p<0.0001$). The SNK test indicated that all 3 treatments, including POR alone, differed from the controls from day 6 onward. There was no significance between the effects of PDL irradiation with and without POR at any time, however.

Figure 4:
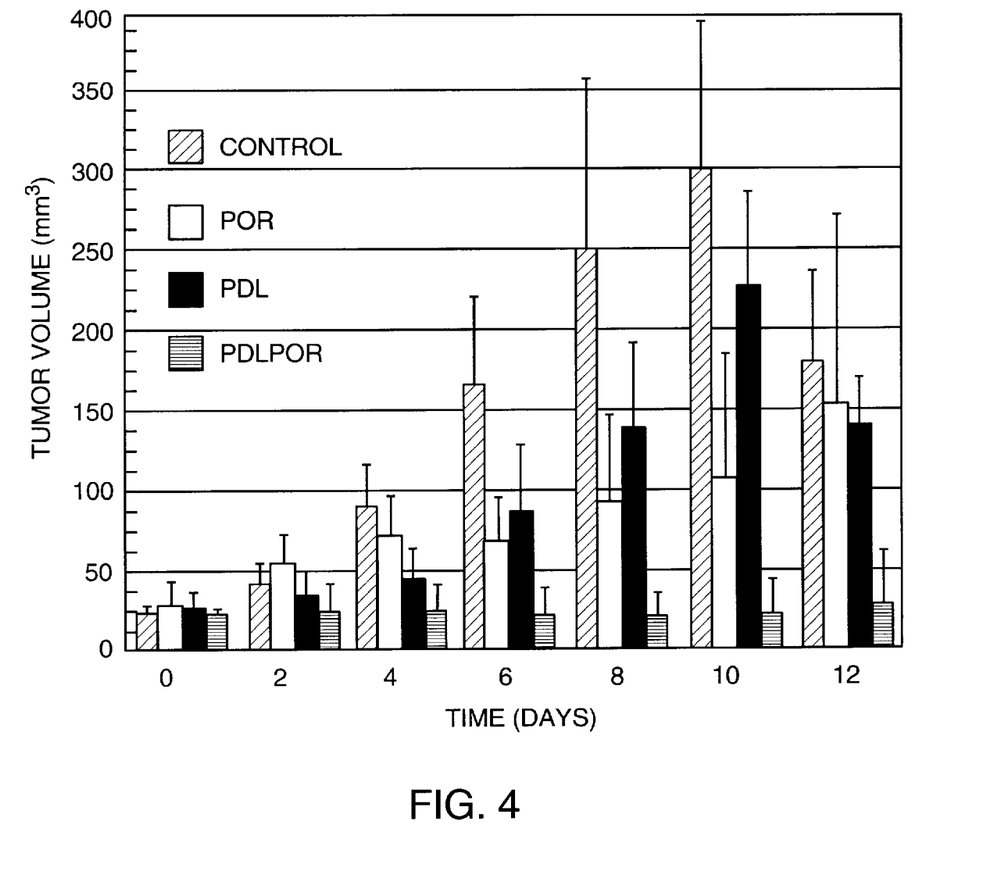
FIG. 4 is a graph of mean tumor volumes of four experimental mouse groups as a function of time after first treatment of the tumor and tumor margin and including only the largest third of tumors measured on day 0, one group including POR only, one group including vascular targeting only, one group including POR with vascular targeting and one control group. Error bars indicate +1 standard deviation.

FIG. 4 shows the results of the experiment of Example VI when only the largest 33% of tumors on day 0 are included in the analysis. This subset of tumors has a mean volume of 23.9 mm$^3$ and SD of 8.2 mm$^3$ on day 0. In contrast to the all-inclusive analysis, the SNK tests here shows no difference between the control and PDL groups at any point in time, and does demonstrate a significant difference between PDL with and without POR at all days after day 6.

Both the area of irradiation and fluence were increased in Example VI relative to Example V experiments. In the majority of animals this treatment resulted in a darkening of skin tissue overlying the tumor, beginning on day 3, that was suggestive of epithelial injury. There was no tissue sloughing. By day 10, these darkened areas exhibited near normal pigmentation with minimal scarring.

EXAMPLE VII

POR with PDL Treatment of Normal Skin Tissue

The effect on normal skin tissue of PDL irradiation with or without POR was determined using 6 adult Syrian golden hamsters. The hamsters were divided into two groups, and hair of each animal was shaved from an area of the flank. One group was irradiated with the PDL 15 min. after ip injection of POR, and the other group was irradiated without POR administration. Biopsies of treated sites were taken 10 min. or 2 days after irradiation. Specimens were fixed with formalin, embedded in paraffin, sectioned, and stained (H&E) for histologic evaluation.

The acute and delayed results of PDL irradiation of hamster skin after administration of POR were observed as a result of histologic studies. Damage appeared limited to the larger microvessels visible at the magnification. Clinically, there was production of slight purpura beginning a few minutes after PDL irradiation that had largely resolved by day 2. Regardless of whether POR had been administered, there was no microscopic or clinical evidence of epithelial necrosis or other damage to tissue structures beyond the blood vessels resulting from single PDL irradiation sufficient to damage microvessels in this animal model.

It is significant that normal skin was unaffected by administration of POR before PDL irradiation, at laser fluences sufficient to cause microvascular damage. Hypoxia-induced cytotoxicity would be an adverse effect if occurring in normal tissue. Most blood vessels in the papillary dermis of normal human skin have outer diameters of 17 to 22 $\mu$m and only a small fraction of blood vessels 20 $\mu$m or smaller can be damaged by the pulsed dye laser. Consequently, the degree of hypoxia induced in normal skin by irradiation with the pulsed dye laser is advantageously slight providing for a high degree of selectivity of photothermal vascular targeting for tumor tissue using bioreductive agent administration.

EXAMPLE VIII

PDL and POR on Human Squamous Cancer Cells

Figure 5:
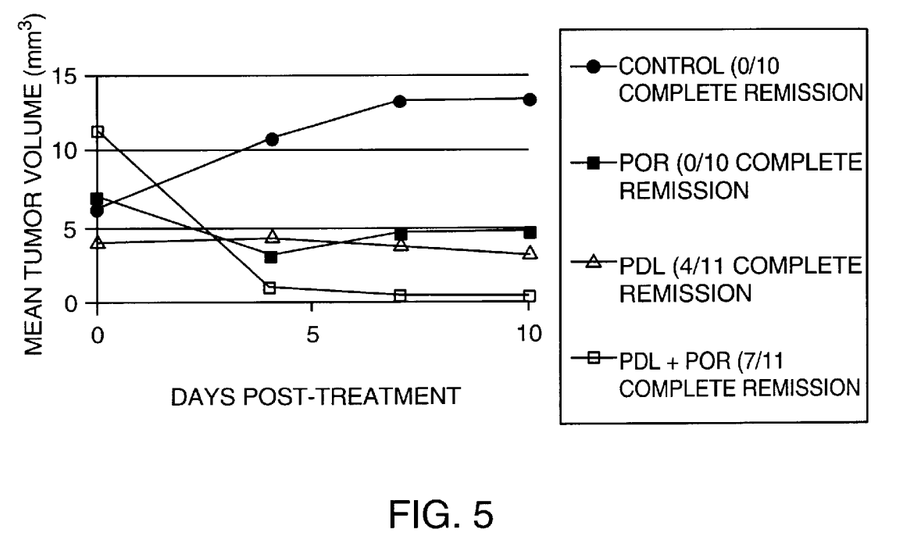
FIG. 5 is a graph of mean tumor volume of four experimental hamster groups as a function of time after first treatment of the tumor and tumor margin, one group including POR only, one group including vascular targeting only, one group including POR with vascular targeting and one control group.

In this example, tumors were produced in the cheek pouches of hamsters by transplantation of human squamous cancer cells according to methods well known in the art. Hamsters were divided into four treatment groups: (1) control, (2) bioreductive agent porfiromycin only (POR), (3) 588 nm pulsed dye laser only (PDL), and (4) combined PDL and POR. The results are presented in FIG. 5 which demonstrates that tumor regression and remission following laser vascular targeting is enhanced by administration of a bioreductive cytotoxin.

What is claimed is:

1. A method of treating a tumor characterized by nutrient-providing blood vessels comprising
   irradiating the tumor or nutrient providing blood vessels in the presence of a bioreductive agent,
   creating an environment of hypoxia for the bioreductive agent, and
   allowing the bioreductive agent to act as a cytotoxic agent in a manner to reduce tumor size.

2. A method of treating a tumor characterized by nutrient-providing blood vessels comprising
   exposing the tumor to a bioreductive agent,
   exposing the tumor to a light source,
   denaturing the nutrient-providing blood vessels by exposing the blood vessels to the light source,
   creating an environment of hypoxia for the bioreductive agent, and
   allowing the bioreductive agent to act as a cytotoxic agent in a manner to reduce tumor size.

3. The method of claim 2 wherein said light source is at a wavelength corresponding to that absorbed by endogenous chromophores.

4. The method of claim 3 wherein said wavelength is between about 560 nm to about 610 nm.

5. The method of claim 3 wherein said wavelength is between about 570 nm to about 600 nm.

6. The method of claim 3 wherein said wavelength is between about 585 nm to about 590 nm.

7. The method of claim 2 wherein said bioreductive agent is porfiromycin or mitomycin C.

8. The method of claim 2 wherein said light source has a pulse duration less than a thermal relaxation time of a volume of the tumor and nutrient-providing blood vessels.

9. The method of claim 8 wherein said pulse duration is between about 0.1 msec to about 60 msec.

10. The method of claim 8 wherein said pulse duration is between about about0.1 msec to about 10 msec.

11. The method of claim 8 wherein said pulse duration is between about 0.3 msec to about 0.5 msec.

12. The method of claim 2 wherein said light source is a laser.

13. The method of claim 12 wherein said laser is a pulsed dye laser.

14. The method of claim 13 wherein said pulsed dye laser has a fluence between about 1 $J/cm^3$ to about 30 $J/cm^3$.

15. The method of claim 13 wherein said pulsed dye laser has a fluence between about 5 $J/cm^3$ to about 15 $J/cm^3$.

16. The method of claim 13 wherein said pulsed dye laser has a fluence of about 10 $J/cm^3$.

17. A method of treating a tumor characterized by nutrient-providing blood vessels comprising
    exposing the tumor to a bioreductive agent,
    exposing the nutrient-providing blood vessels to an exogenous photoactivated compound,
    denaturing the nutrient-providing blood vessels by exposing the blood vessels to a light source at a wavelength corresponding to that absorbed by the exogenous photoactivated compound,
    creating an environment of hypoxia for the bioreductive agent, and
    allowing the bioreductive agent to act as a cytotoxic agent in a manner to reduce tumor size.

18. The method according to claim 17, wherein said photoactivated compound is iodocyanine green.

19. The method of claim 17, wherein said photoactivated compound is a bioreductive agent.

20. A method of treating a tumor characterized by nutrient-providing blood vessels comprising
    exposing the tumor to a bioreductive agent,
    denaturing the nutrient-providing blood vessels by exposing the blood vessels to a pulsed dye laser at a wavelength corresponding to that absorbed by endogenous chromophores, wherein said pulsed dye laser has a pulse duration less than a thermal relaxation time of a volume of the nutrient-providing blood vessels,
    creating an environment of hypoxia for the bioreductive agent, and
    allowing the bioreductive agent to act as a cytotoxic agent in a manner to reduce tumor size.

* * * * *